(12) United States Patent
Shtyrlin et al.

(10) Patent No.: US 10,844,018 B2
(45) Date of Patent: Nov. 24, 2020

(54) PYRIDOXINE DERIVATIVE FOR TREATMENT OF EPILEPSY

(71) Applicants: AO "TATKHIMFARMPREPARATY", Kazan (RU); Kazan Federal University, Kazan (RU)

(72) Inventors: Yurij G. Shtyrlin, Kazan (RU); Mikhail S. Dzyurkevich, pos. Donskoe Kaliningrad Obl. (RU); Nikita V. Shtyrlin, Kazan (RU); Elena V. Gerasimova, Kazan (RU); Al'fiya G. Iksanova, Kazan (RU); Guzel' F. Sitdikova, Kazan (RU); Aleksej V. Yakovlev, Kazan (RU)

(73) Assignees: AO "Tatkhimfarmpreparaty", Kazan (RU); Kazan Federal University, Kazan (RU)

( * ) Notice: Subject to any disclaimer, the term of this patent is extended or adjusted under 35 U.S.C. 154(b) by 0 days.

(21) Appl. No.: 16/751,926

(22) Filed: Jan. 24, 2020

(65) Prior Publication Data

US 2020/0157051 A1     May 21, 2020

Related U.S. Application Data

(63) Continuation of application No. PCT/RU2018/000380, filed on Jun. 7, 2018.

(30) Foreign Application Priority Data

Jul. 24, 2017    (RU) ................................ 2017126301

(51) Int. Cl.
    *C07D 213/67*      (2006.01)

(52) U.S. Cl.
    CPC .................................. *C07D 213/67* (2013.01)

(58) Field of Classification Search
    CPC .................................................. C07D 213/67
    USPC ....................................................... 514/347
    See application file for complete search history.

(56) References Cited

FOREIGN PATENT DOCUMENTS

| EA | 026500 B1 | 4/2017 |
| RU | 2010131342 A | 2/2012 |
| WO | 2014085153 A1 | 6/2014 |

OTHER PUBLICATIONS

Mohamad Mikati et al. Pyridoxine-dependent epilepsy:EEG investigations and long term follow-up. Abstract (Year: 1991).*
Stephen Coburn et al Identification of Pyridoxine 3-sulfate, Pyridoxal 3-sulfate, and N-methylpyridoxine as Major Urinary Metabolites of Vitamin B6 in Domestic cats. (Year: 1987).*
Nikita Shtyrlin et al . Synthesis of novel 6-substituted sulfur-containing derivatives of pyridoxine. (Year: 2012).*
International Search Report from PCT/RU2018/000380 dated Jun. 7, 2018, dated Oct. 4, 2018.
Asif, Mohammad, Role of various vitamins in the patents with epilepsy, International Journal of Pharmacological Research, 2013, pp. 1-9, vol. 3, Issue 1.
Valproic Acid, Sodium Salt, Material Safety Data Sheet, Issue Date: Oct. 18, 2010, http://datasheets.scbt.com/sc202378.pdf.
Carbamazepine, Material Safety Data Sheet, Issue Date Feb. 1, 2010, http://datasheets.scbt.com/sc202518.pdf.
Phenobarbital, Safety Data Sheet, Preparation Date Aug. 26, 2016, http:www.sciencelab.com/msds.php?msdsId=9926461.
Phenytoin Sodium Capsules, Safety Data Sheet, Revision Date May 16, 2016, http://www.pfizer.com/system/files/products/material_safety_data/PHENYTOIN%20SODIUM%20OSOLN.pdf.
Ethosuximide Capsules, Safety Data Sheet, Revision Date Apr. 13, 2015, http:www.pfizer.com/files/products/material_safety_data/ETHOSUXIMIDE%20CAPSULES.pdf.
Lamictal XR, Safety Data Sheet, Issue Date Dec. 19, 2014, http://www.msds-gsk.com/GetSdsFile.ashx?fileId=5508.
Topiramate, Safety Data Sheet, Preparation Date Oct. 11, 2019, https://fagron.com/sites/default/files/document/msds_coa/97240-79-4_(USA).pdf.
Levetiracetam, Safety Data Sheet, Refision Date Nov. 26, 2012, U.S. Pharmacopeia, https://www.akron.com/documents/catalog/msds/50383-241-16.pdf.
Levetiracetam, Safety Data Sheet, Revision Date Feb. 20, 2019, Cayman Chemical Company, https://www.caymanchem.com/msdss/9001820m.pdf.
Gabapentin Tablets (Neurontin), Material Safety Data Sheet, Revision Date Apr. 7, 2010, http://www.pfizer.com/system/files/products/material_safety_data/PZ01158.pdf.

(Continued)

*Primary Examiner* — Rita J Desai
(74) *Attorney, Agent, or Firm* — Patentbar International, P.C.

(57) ABSTRACT

A pyridoxine-based compound of formula 1:

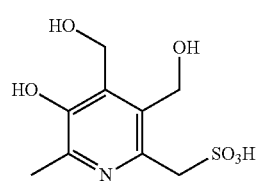

exhibits a high level of antiepileptic activity. At doses of 25, 50 and 100 mg/kg, compound 1 completely suppresses the epileptic electrical activity of the brain within an hour after intraperitoneal administration to rats on the penicillin model of epilepsy. The rats' corazol model of epilepsy shows a decrease in intensity and duration of seizures with the administration of compound 1 at doses of 25 and 100 mg/kg intraperitoneally and 100 and 200 mg/kg orally, and the complete prevention of seizures in some cases at a dosage of 250 mg/kg with oral administration. Compound 1 is low toxic. The $LD_{50}$ parameter in rats exceeds 2000 and 5000 mg/kg of body weight with intraperitoneal and oral administration respectively. The technical solution provides a new highly effective and safe drug for the treatment of epilepsy.

2 Claims, 2 Drawing Sheets

(56) References Cited

OTHER PUBLICATIONS

Zonisamide, Material Safety Data Sheet, Issue Date Dec. 17, 2009, http://datasheets.scbt.com/sc203316.pdf.
Mironov A.N., et al., Guidelines for Carrying Out Pre-Clinical Studies of Drugs, 2012, pp. 240, pp. 244-245, Moscow.
Shtyrlin N.V. et al, New Synthetic Method for 2,3,4-Tris(hydroxymethyl)-6-methylpyridin-5-ol, Russian Journal of Organic Chemistry, 2009, pp. 1266-1268, vol. 45, No. 8, Pleiades Publishing, Ltd.
Brenner, G. M., Stevens, C.W., Pharmacology, 4th Edition, 2013, Elsevier/Saunders.

* cited by examiner

Table 1

Antiepileptic properties of compound 1 on the penicillin model of epilepsy on rats

| Time from "reference point", minutes | Penicillin without treatment (n = 5) | Sodium valproate 600 mg/kg (n = 4) | 1, 25 mg/kg (n = 2) | 1, 50 mg/kg (n = 3) | 1, 100 mg/kg (n = 2) |
|---|---|---|---|---|---|
| | Characteristics of HAED (amplitude,%/frequency,%) | | | | |
| 5 | 121±6 / 94±12 | 100±8 / 47±51 | 68±3 / 79±9 | 98±27 / 101±4 | 95±1 / 106±14 |
| 30 | 85±11 / 92±17 | 81±9 / 67±22 | 49±2 / 66±20 | 39±10 / 44±8 | 87±2 / 73±33 |
| 60 | 69±13 / 31±44 | 60±14 / 58±34 | HAED are not observed | HAED are not observed | HAED are not observed |

Fig. 1

Table 2

Antiepileptic properties of compound 1 on the corazol model of epilepsy on rats

| Characteristics of seizures | Dosage of compound 1 | | | | | |
|---|---|---|---|---|---|---|
| | Control (n = 6) | 25 mg/kg ip (n = 4) | 100 mg/kg ip (n = 5) | 100 mg/kg oral (n = 3) | 200 mg/kg oral (n = 4) | 250 mg/kg oral (n = 4) * |
| Time before the onset of seizures (min); | 13,5±5,4 | 11,8±2,6 | 16,3±2,7 | 10,2±2,2 | 10,5±1,5 | 7,2±1,1 |
| Duration of seizures, s | 38,6±2,2 | 24,6±3,6 | 26,4±4,8 | 21,5±0,5 | 19,7±4,3 | 12,5±1,2 |
| Seizure intensity, points | 5,1±0,3 | 4,5±0,2 | 4.0 | 4,5±0,5 | 3,8±0,3 | 3,0±0,5 |
| Number of animals with repeated convulsions | 5 | 1 | 0 | 1 | 0 | 0 |
| Number of dead animals | 2 | 0 | 0 | 0 | 0 | 0 |

* At a dosage of 250 mg / kg of compound 1, convulsions developed in only two animals out of four

Fig.2

PYRIDOXINE DERIVATIVE FOR TREATMENT OF EPILEPSY

RELATED APPLICATIONS

This Application is a Continuation application of International Application PCT/RU2018/000380, filed on Jun. 7, 2018, which in turn claims priority to Russian Patent Application RU2017126301, filed Jul. 24, 2017, both of which are incorporated herein by reference in their entirety.

FIELD OF THE INVENTION

The invention refers to physiologically active substances—pyridoxine derivatives, namely, the compound of formula 1, having antiepileptic activity.

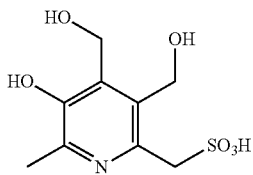

BACKGROUND OF THE INVENTION

Epilepsy is one of the most common chronic diseases of the nervous system in the world, affecting both children and adults. According to WHO, about 50 million people suffer from epilepsy, or about 0.5-1% of the world's population. Every year around 2.5 million new cases are diagnosed worldwide. 30% of patients with epilepsy are pharmacoresistant.

From the investigated prior art, the applicant has not identified technical solutions which are analogues of the claimed technical solution by the chemical structure.

From the investigated prior art, the applicant identified known technical solutions which are analogues of the claimed technical solution by the intended purpose, namely antiepileptic drugs.

In accordance with modern international practice, all currently available antiepileptic drugs (AED) are divided into:
  old (phenobarbital and diphenine);
  intermediate (succinimides and benzodiazepines);
  basic (valproates and carbamazepine);
  new (lamotrigine, topiramate, oxcarbazepine, levetiracetam, tiagabine, gabapentinum, felbamate, pregabalinum, zonisamide).

Of the above drugs, valproic acid preparations (valproate) and carbamazepine group drugs are currently used most often and are considered to be "first choice" drugs (basic drugs).

The drug Depakine (Sanofi-Aventis, France) is known. Active substance: valproic acid. Indications for use: generalized epileptic seizures—clonic, tonic, tonic-clonic, absences, myoc Ionic, atonic; Lennox-Gastaut syndrome; partial epileptic seizures with or without secondary generalization (in monotherapy or in combination with other antiepileptic drugs). It is allowed to be used in pediatrics.

The disadvantage of the known drug are the following side effects: drowsiness, disorders of the gastrointestinal tract, hepatotoxicity, pancreotoxicity, nausea, weight gain. [Stevens G. M. Pharmacology/G. M Stevens, C. W. Brenner—Philadelphia: Elsevier/Saunders, 2013.—519c. (https://books.google.ru/books?id=Cd39SN6OBiMC&pg=PA204&redir_esc=y#v=onepage &q&f=false)]. Acute toxicity in mice (sodium valproate) with oral administration $LD_{50}$: 977 mg/kg, with intraperitoneal administration $LD_{50}$: 470 mg/kg (http://datasheets.scbt.com/sc-202378.pdf).

The drug Finlepsin (AWD.pharma, Germany) is known. Active substance: carbamazepine. Indications for use: epilepsy—partial seizures with elementary symptoms (focal seizures), partial seizures with complex symptoms, psychomotor seizures, grands convulsive mals of mainly focal origin (grands mals during sleep, diffuse grands mals), mixed forms of epilepsy; trigeminal neuralgia; idiopathic neuralgia of the glossopharyngeal nerve; pain in diabetic polyneuropathy; epileptiform convulsions in multiple sclerosis, facial spasms in trigeminal neuralgia, tonic convulsions, paroxysmal dysarthria and ataxia, paroxysmal paresthesias and bouts of pain; alcohol withdrawal syndrome (anxiety, convulsions, hyper excitability, sleep disturbances); psychotic disorders (affective and schizoaffective disorders, psychoses, dysfunctions of the limbic system). It is allowed to be used in pediatrics.

The disadvantage of the known drug are the following side effects: drowsiness, lethargy and other signs of depression of the central nervous system, ataxia, nausea, rarely—aplastic anemia. [Stevens G. M. Pharmacology/G. M Stevens, C. W. Brenner—Philadelphia: Elsevier/Saunders, 2013.—519c. (https://books.google.ru/books?id=Cd39SN6OBiMC&pg=PA204&redir_esc=y#v=onepage &q&f=false)]. Acute toxicity in mice (carbamazepine) with oral administration $LD_{50}$: 529 mg/kg, with intraperitoneal administration $LD_{50}$: 114 mg/kg (http://datasheets.scbt.com/sc-202518.pdf).

The drug Phenobarbital (JSC Dalhimpharm, Russia) is known. Active substance: phenobarbital. Indications for use: epilepsy—generalized tonic-clonic seizures, focal seizures in adults and children; chorea; spastic paralysis; various convulsive reactions; as a sedative in small doses in combination with other drugs (antispasmodics, vasodilators) for neuro-vegetative disorders; as a sleeping pill. It is allowed to be used in pediatrics.

The disadvantage of the known drug are the following side effects: ataxia, decreased mental ability, drowsiness, dizziness, development of addiction, rash, respiratory depression. [Stevens G. M. Pharmacology/G. M Stevens, C. W. Brenner—Philadelphia: Elsevier/Saunders, 2013.—519c. (https://books.google.ru/books?id=Cd39SN6O BiMC&pg=PA204&redir_esc=y#v=onepage &q&f=false)]. Acute toxicity in rats (phenobarbital) with oral administration $LD_{50}$: 163 mg/kg (http://www.sciencelab.com/msds.php?msdsId=9926461).

The drug Diphenine (Usolye-Siberian CPP, Russia) is known. Active substance: phenytoin. Indications for use: epilepsy (grands mals); epileptic status with tonic-clonic seizures; epileptic seizures in neurosurgery (prevention and treatment); ventricular arrhythmias (including with glycosidic intoxication or tricyclic antidepressants associated with intoxication); trigeminal neuralgia (as a second-line agent or in combination with carbamazepine). It is allowed to be used in pediatrics.

The disadvantage of the known drug are the following side effects: digestive disorders, gingival hyperplasia, megaloblastic anemia and other manifestations of red blood cell deficiency, osteomalacia, psychiatric manifestations. [Stevens G. M. Pharmacology/G. M Stevens, C. W. Brenner—Philadelphia: Elsevier/Saunders, 2013.—519c. (https:// books.google.ru/books?id=Cd39SN6OBiMC&pg=PA204& redir_esc=y#v=onepage&q&f=false)]. Acute toxicity in mice (sodium phenytoin) with oral administration $LD_{50}$: 165 mg/kg (http://www.pfizer.com/system/files/products/material_safety_data/PHENYTOIN%20SODIUM%20SOLN.pdf).

The drug Suxilep (Delpharm Lille S.a.S., France) is known. Active substance: ethosuximide. Indications for use: seizures of pycnoleptic absences; complex and atypical convulsive seizures; myoclonic-astatic petits mals; juvenile myoclonic seizures (impulsive petits mals). Not recommended for use for children under 6 years.

The disadvantage of the known drug are the following side effects: drowsiness, dizziness, digestive disorders, lethargy and nausea. [Stevens G. M. Pharmacology/G. M Stevens, C. W. Brenner—Philadelphia: Elsevier/Saunders, 2013.—519c. (https://books.google.ru/books?id=Cd39 SN6OBiMC&pg=PA204&redir_esc=y#v=onepage&q&f= false)]. Acute toxicity in mice (ethosuximide) with oral administration $LD_{50}$: 1530 mg/kg (http://www.pfizer.com/ files/products/material_safety_data/ETHOSUXIMIDE% 20CAPSULES.pdf).

The drug Lamitor (Torrent Pharmaceuticals, India) is known. Active substance: lamotrigine. Indications for use: epilepsy—partial and generalized seizures, including tonic-clonic seizures, as well as seizures with Lennox-Gastaut syndrome as part of combination therapy or monotherapy. It is allowed to be used in pediatrics.

The disadvantage of the known drug are the following side effects: ataxia, diplopia, dizziness, drowsiness, headache, nausea, rash, Stevens-Johnson syndrome. [Stevens G. M. Pharmacology/G. M Stevens, C. W. Brenner—Philadelphia: Elsevier/Saunders, 2013.—519c. (https://books.google.ru/books?id=Cd39SN6OBiMC&pg=PA204&redir_ esc=y#v=onepage &q&f=false)]. Acute toxicity in mice (lamotrigine) with oral administration $LD_{50}$: 269 mg/kg (http://www.msds-gsk.com/GetSdsFile.ashx?fileld=5508).

The drug Topiramate (ALSI Pharma, Russia) is known. Active substance: topiramate. Indications for use: monotherapy in adults and children from 6 years of age with partial (with or without secondary generalization) or primary generalized tonic-clonic seizures; complex therapy in adults and children over 3 years of age with partial with or without secondary generalization or generalized tonic-clonic seizures, as well as for the treatment of seizures due to Lennox-Gastaut syndrome; prevention of migraine attacks in adults.

The disadvantage of the known drug are the following side effects: ataxia, dizziness, drowsiness, nystagmus, paresthesia, psychomotor disturbances. [Stevens G. M. Pharmacology/G. M Stevens, C. W. Brenner—Philadelphia: Elsevier/Saunders, 2013.—519c. (https://books.google.ru/ books?id=Cd39SN6OBiMC&pg=PA204&redir_esc=y#v= onepage &q&f=false)]. Acute toxicity in rats (topiramate) with oral administration $LD_{50}$: 3570 mg/kg (https://fagron.com/sites/default/files/document/msds_coa/97240-79-4_(USA).pdf).

The drug Levetinol (Actavis hf., Iceland) is known. Active substance: levetiracetam. Indications for use: partial convulsions with or without secondary generalization in patients from 16 years old with newly diagnosed epilepsy; myoclonic convulsions in patients with juvenile myoclonic epilepsy from 12 years old; primary generalized tonic-clonic convulsions in patients with idiopathic generalized epilepsy from 12 years old.

The disadvantage of the known drug are the following side effects: drowsiness, weakness and dizziness. [Stevens G. M. Pharmacology/G. M Stevens, C. W. Brenner—Philadelphia: Elsevier/Saunders, 2013.—519c. (https://books.google.ru/books?id=Cd39SN6OBiMC&pg=PA204& redir_esc=y#v=onepage &q&frfalse)]. Acute toxicity in mice (levetiracetam) with oral administration $LD_{50}$: >5000 mg/kg (http://www.akom.com/documents/catalog/msds/ 50383-241-16.pdf) with intravenous injection $LD_{50}$: 1081 mg/kg (https://www.caymanchem.com/msdss/9001820m.pdf).

The drug Tebantin (Gedeon Richter, Hungary) is known. Active substance: gabapentinum. Indications for use: partial convulsions with or without secondary generalization in adults and children over 12 years old as monotherapy or adjunctive therapy; partial convulsions with or without secondary generalization in children from 3 to 12 years of age as an additional therapy; neuropathic pain in patients older than 18 years.

The disadvantage of the known drug are the following side effects: ataxia, drowsiness, dizziness, nystagmas and limb trembling. [Stevens G. M. Pharmacology/G. M Stevens, C. W. Brenner—Philadelphia: Elsevier/Saunders, 2013.—519c. (https://books.google.ru/books?id=Cd39 SN6OBiMC&pg=PA204&redir_esc=y#v=onepage&q& f=false)]. Acute toxicity in mice (gabapentinum) with oral administration $LD_{50}$: >5000 mg/kg; with intravenous injection $LD_{50}$: 1000-2000 mg/kg (http://www.pfizer.com/system/files/products/material_safety_data/PZ01158.pdf).

The drug Lyric (Pfizer Manufacturing Deutschland, Germany) is known. Active substance: pregabaline. Indications for use: neuropathic pain in adults; epilepsy (as an adjunctive therapy in adults with partial convulsive seizures, with or without secondary generalization); generalized anxiety disorder in adults; fibromyalgia in adults. It is not used in pediatrics.

The disadvantage of the known drug are the following side effects: drowsiness, visual impairment, weight gain, impaired coordination of movements. [Stevens G. M. Pharmacology/G. M Stevens, C. W. Brenner—Philadelphia: Elsevier/Saunders, 2013.—519c. (https://books.google.ru/ books?id=Cd39SN6OBiMC&pg=PA204&redir_esc=y#v= onepage&q&f=false)]. Acute toxicity in rats (gabapentinum) with oral administration $LD_{50}$: >5000 mg/kg; with intravenous injection $LD_{50}$: >300 mg/kg (http://www.pfizer.com/system/files/products/material_safety_data/PZ01158.pdf).

The drug Zonegran (Eisai Co. Ltd., Japan) is known. Active substance: zonisamide. Indications for use: monotherapy in patients with partial epileptic seizures with or without secondary generalization, with first diagnosed epilepsy; as part of adjunctive therapy in adults, adolescents, and children from 6 years of age with partial seizures with or without secondary generalization.

The disadvantage of the known drug are the following side effects: headache, dizziness, drowsiness, anorexia, nausea, at an early age—metabolic acidosis. [Stevens G. M. Pharmacology/G. M Stevens, C. W. Brenner—Philadelphia: Elsevier/Saunders, 2013.—519c. (https://books.google.ru/ books?id=Cd39SN6OBiMC&pg=PA204&redir_esc=y#v= onepage &q&frfalse)]. Acute toxicity in mice (zonisamide) with oral administration $LD_{50}$: 1829 mg/kg, with intraperitoneal administration $LD_{50}$: 699 mg/kg (http://datasheets.s-cbt.com/sc-203316.pdf).

Thus, the general disadvantages of known drugs are: the presence of significant side effects, the immunity of the symptoms of the disease to treatment, as well as the high cost of treatment. Today, there is a great need to create and introduce into clinical practice new, effective and safe drugs for the treatment of epilepsy.

SUMMARY OF THE INVENTION

The objective of the claimed technical solution is to obtain a new compound with high antiepileptic activity and which has no analogues in the world in chemical structure.

The technical result of the proposed invention is a new antiepileptic compound based on pyridoxine, which has the ability to effectively stop epileptic seizures.

The problem is solved, and the specified technical result is achieved by obtaining the claimed new compound of formula 1, with the ability to effectively reduce the epileptic activity of the brain.

The claimed compound is obtained through a three-stage synthesis from the starting 6-hydroxymethyl derivative of pyridoxine 2 according to the scheme below:

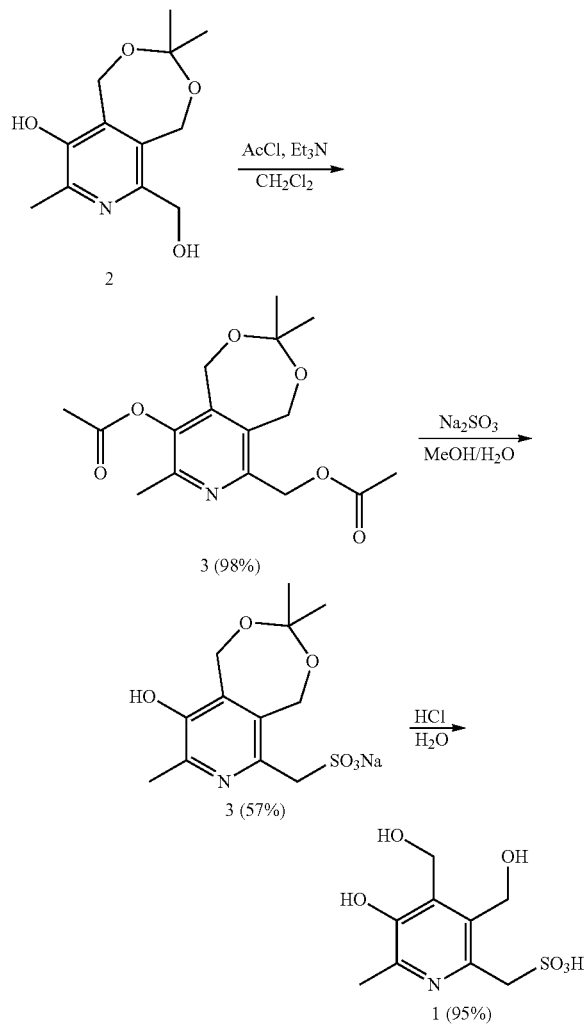

The structures of the obtained compounds are confirmed by the methods of mass spectrometry, $^1H$ and $^{13}C$ NMR spectroscopy. NMR spectra are recorded on the Bruker AVANCE-400 device. The chemical shift is determined with respect to the signals of residual protons of deuterated solvents ($^1H$ and $^{13}C$). Melting temperatures are determined using Stanford Research Systems MPA-100 OptiMelt. Control over the course of reactions and purity of compounds is carried out by TLC method on Sorbfil Plates. An ultra-high resolution HPLC/MS experiment is carried out using a TripleTOF 5600 mass spectrometer, AB Sciex (Germany).

Penicillin and corazol, which, as is known from the prior art, are capable of causing epileptic seizures when they enter the central nervous system, were taken as drugs causing epileptic seizures [Mironov A. N., Bunatyan N. D. et al. Rukovodstvo po provedeniyu doklinicheskikh issledovaniy lekarstvennykh sredstv. [Guidelines for Pre-clinical Drug Research].

BRIEF DESCRIPTION OF THE DRAWINGS

The claimed technical solution is illustrated in FIG. 1. and FIG. 2.

FIG. 1 presents Table 1, which shows data on the antiepileptic properties of the compound 1 in the penicillin rat epilepsy model.

FIG. 2 presents Table 2, which shows data on the antiepileptic properties of the compound 1 in the corazol rat epilepsy model.

DETAILED DESCRIPTION OF THE PREFERRED EMBODIMENTS

The claimed technical solution is illustrated by the following examples of specific performance.

Example 1. Synthesis of (5-hydroxy-3,4-bis (hydroxymethyl)-6-methylpyridin-2-yl) methanesulfonic acid (1)

Compound 1 is obtained in 3 stages from the starting compound (2).

Stage 1. A portion of 100.0 g (0.418 mol) of 6-(hydroxymethyl)-3,3,8-trimethyl-1,5-dihydro-[1,3] dioxepino [5,6-c] pyridin-9-ol (2) is suspended in 1000 ml of dichloromethane [Shtyrlin N. V. Novyy metod sinteza 6-metil-2,3,4-tris (gidroksimetil)piridin-5-ola [A new method for the synthesis of 6-methyl-2,3,4-tris (hydroxymethyl) pyridin-1-ol]/N. V. Shtyrlin, A. D. Strelnik, L. P. Sysoeva, O. A. Lodochnikova, E. N. Klimovitsky, Y. G. Shtyrlin//Zhurn.org.khimii. [Journal of organic chemistry] 2009.—Vol. 45, Publ. 8.—P. 1274-1275.]. 145.0 ml (1.045 mol) of triethylamine are added in one portion to the resulting suspension, when stirring, followed by dropwise 74.2 ml (1.045 mol) of acetyl chloride. The reaction mixture is stirred for 2 hours at room temperature. After that, the solution is washed three times with 500 ml of water. The organic fraction is dried over magnesium sulfate, filtered and evaporated on a rotary evaporator to give 132.0 g (98%) of (9-acetoxy-3,3,8-trimethyl-1,5-dihydro-[1,3] dioxepino [5,6-c] pyridin-6-yl) methyl acetate (3).

Stage 2. A portion of (9-acetoxy-3,3,8-trimethyl-1,5-dihydro [1,3] dioxepino [5,6-c] pyridin-6-yl) methyl acetate (3) from the previous stage (132.0 g, 0.408 mol) is dissolved in 700 ml of methyl alcohol. A solution of 127.0 g (1.225 mol) of sodium sulfite in 900 ml of water is separately prepared. The resulting solutions are poured together and stirred at room temperature for 4 hours. Then the mixture is neutralized with hydrochloric acid to pH=7.0 and evaporated on a rotary evaporator. The dry distillation residue is extracted with 600 ml of hot n-propyl alcohol and filtered. Upon cooling, from the filtrate precipitates a product, which is filtered off, washed 3 times with 50 ml of cold n-propanol and dried to obtain 75.9 g (57%) of (9-hydroxy-3,3,8-trimethyl-1,5-dihydro-[1,3] dioxepino [5,6-c] pyridin-6-yl) sodium methanesulfonate (4). Melting point is 197° C. with decomp. NMR spectrum $^1$H (400 MHz, DMSO-d$_6$), δ, ppm: 1.38 (s, 6H, C(CH$_3$)$_2$); 2.30 (s, 3H, CH$_3$); 3.82 (s, 2H, CH$_2$—S); 4.79 (s, 2H, CH$_2$); 4.90 (s, 2H, CH$_2$). NMR $^{13}$C {$^1$H} (100 MHz, DMSO-d$_6$), δ, ppm: 19.28; 23.73; 57.47; 59.11; 60.97; 101.45; 132.07; 134.18; 140.97; 143.25; 146.78. HRMS-ESI: found [M+H]$^+$ 326.0669, [M+Na]$^+$ 348.0488, C$_{12}$H$_{16}$NNaO$_6$S, calculated [M+H]$^+$ 326.0669, [M+Na]$^+$ 348.0488.

Stage 3. A portion of (9-hydroxy-3,3,8-trimethyl-1,5-dihydro [1,3] dioxepino [5,6-c] pyridin-6-yl) sodium methanesulfonate (4) from the previous stage (75.9 g 0.233 mol) is dissolved in 500 ml of water. The resulting solution is brought to pH=1 with concentrated hydrochloric acid. The reaction mixture is left for 3 hours at room temperature, then evaporated on the rotary evaporator. The dry residue is extracted with 200 ml of cold hydrochloric acid and filtered. 700 ml of isopropanol is added to the filtrate. In the cold from the mixture falls a crystalline precipitate, which is filtered and washed 3 times with 30 ml of cold isopropanol and dried to obtain the desired product –60.8 g (95%) of (5-hydroxy-3,4-bis (hydroxymethyl)-6-methylpyridine-2-yl) methanesulfonic acid (1). T. decomp. is 250° C. NMR $^1$H (400 MHz, DMSO-d$_6$), δ, ppm: 2.56 (s, 3H, CH$_3$); 4.27 (s, 2H, CH$_2$—S); 4.70 (s, 2H, CH$_2$); 4.90 (s, 2H, CH$_2$). NMR $^{13}$C {$^1$H} (100 MHz, DMSO-d$_6$), δ, ppm: 14.74; 51.57; 55.52; 56.19; 136.44; 138.79; 141.50; 142.95; 151.62. HRMS-ESI: found [M+H]$^+$ 264.0536, C$_9$H$_{13}$NO$_6$S, calculated [M+H]$^+$ 264.0536.

Example 2. Study of the Effect of Compound 1 on the Electrical Activity of the Brain in Epileptic Seizures (Using the Penicillin Model of Epilepsy as an Example)

Experiments were carried out on male Wistar rats with a body weight of 180-250 g.

Under isoflurane anesthesia (1.5%), surgical preparation for the experiment is performed. Urethane (1.5 mg/kg) is used for anesthesia during the experiment. Next, the animal is fixed in a stereotactic installation. 2×2 mm holes are drilled in the skulls of animals over symmetrical areas of the sensorimotor cortex of the brain and a 16-channel silicon-based probe (Neuronexus) is installed with a step of 100 µm between the recording electrodes to divert electrical activity from these areas. A silver chloride electrode, which serves as a combined ground electrode and a reference electrode, is introduced into the cerebellum or the visual cortex to a depth of 2-3 mm.

To create a focus of epileptic activity in parallel to the somatosensory zones, 2×2 mm holes are drilled in the area of the visual cortex, into which 10 µl of a solution of sodium salt of benzylpenicillin are applied at a concentration of 40,000 IU/ml.

Compound 1 at a dose of 100 mg/kg, 50 mg/kg, 25 mg/kg is administered intraperitoneally (ip) in the presence of stable epileptiform activity 30 minutes after the application of penicillin. The amplitude-frequency characteristics of epileptiform activity are evaluated.

As a comparison substance, sodium valproate 600 mg/kg is used, which is administered ip in the presence of stable epileptiform activity.

For statistical processing of experimental data, statistical programs Origin 8.5 and IBM SPSS Statistics are used.

The significance of differences between populations is evaluated by the Mann-Whitney U-test.

The results of the applicant's experiments as in Example 2 show the following.

2-3 minutes after the intracranial application of penicillin, the appearance of sharp high-amplitude waves (1000-20000 µV) on the electroencephalogram is observed with a frequency of 20 to 70 min-1. High-amplitude electric discharges (HAED) caused by penicillin are observed during three hours of registration. Their presence, frequency and amplitude are characteristic indicators of brain epileptic activity.

The effect of penicillin after 30 minutes of action is equated to 100% and is called the "reference point", starting with which the test compounds are administered (the claimed compound and the reference drug—sodium valproate).

The characteristics of HAED 5, 30, and 60 minutes after the reference point are shown in Table 1 in FIG. 1.

From the data of Table 1 it is seen that the introduction of the claimed compound 1 leads to a decrease in the amplitude and frequency of HAED, completely suppressing HAED in the animal 60 minutes after administration.

Administration of sodium valproate does not completely suppress HAED.

From the foregoing, we can conclude that the antiepileptic effect of the claimed compound 1 at a dose of 25, 50, 100 mg/kg is much more pronounced than that of the comparison drug—sodium valproate, since the administration of sodium valproate even at a dose of 600 mg/kg does not lead to a complete suppression of HAED. Thus, the antiepileptic effect of the claimed compound is higher, compared with sodium valproate, not less than 6-24 times.

Example 3. Study of the Effect of Compound 1 on the Development of Seizures (Using the Corazol Model of Epilepsy as an Example)

Experiments were carried out on male Wistar rats with a body weight of 180-250 g.

Corazol at a dose of 80 mg/kg is administered subcutaneously in the cervical area of the back. Animals were observed for 60 min after injection of corazol with the registration of the main indicator—the first generalized clonic seizures with loss of the overturning reflex.

The intensity of the development of a convulsive seizure was studied on a 6-point scale:
  0—lack of convulsive activity;
  1—hyperkinesia;
  2—trembling, twitching, excessive grooming, stereotypical movements;
  3—clonic convulsions of the front legs with lifting on the hind legs;
  4—pronounced tonic-clonic convulsions, the fall of the animal to the side, the presence of a phase of tonic extensia;
  5—repeated tonic-clonic convulsions, loss of posture;
  6—complete tonic attack with apnea, death of the animal.

To study the effect of the claimed compound 1 on the development of convulsions caused by corazol, compound 1 is dissolved in physiological saline and administered as follows:
  at doses of 25 mg/kg, 100 mg/kg intraperitoneally (ip) 30 minutes before the induction of convulsions with corazol;

at doses of 100 mg/kg, 200 mg/kg, 250 mg/kg intragastrically 1 hour before the induction of convulsions with corazol.

The development of convulsive disorder is assessed by the following indicators:
time before the onset of seizures (min);
duration of seizures (sec.);
intensity of seizures on a 6-point scale;
number of animals with repeated convulsions;
number of dead animals in the group.

For statistical processing of experimental data, statistical programs Origin 8.5 and IBM SPSS Statistics are used.

The significance of differences between populations is evaluated by the Mann-Whitney U-test.

The results of a study of the effect of compound 1 on the development of convulsions caused by corazol are shown in Table 2 in FIG. 2.

As can be seen from the data shown in Table 2, the results of the experiment as in Example 3 show a pronounced antiepileptic activity of compound 1 in the corazole model of rat epilepsy both in the oral and intravenous ways of administration, which is expressed in a dose-dependent decrease in the duration and intensity of seizures.

In addition, in all dosages, compound 1 greatly reduces the likelihood of recurrence of seizures, and also completely prevents deaths.

The best results in reducing the development of a seizure after the administration of corazol are observed with oral administration of compound 1 at a dose of 250 mg/kg. At concentrations of 100 and 200 mg/kg, the effect of the claimed compound 1 is slightly less pronounced.

Example 4. Determination of Acute Toxicity in Mice with Oral Administration

The study was performed on mice of the CD-1 (ICR) line (6-8 weeks, weight not less than 18 g, females). Two-fold intragastric (oral) administration of compound 1 in a volume of not more than 0.5 ml/30 g of body weight of the mouse using a gastric tube was used.

The introduction was carried out to animals deprived of food (for a period of not less than 8 hours) with free access to water. The volume of administration was calculated individually for each animal, based on the body mass recorded immediately before the introduction of the substance. Access to water and feed was renewed one hour after administration.

To prepare a dose of 5000 mg/kg for administration to mice, a portion of 1.5 g of compound 1 in a polystyrene boat on a Vibra scale (Shinko Denshi, Japan) was weighed, transferred to a volumetric flask of accuracy class A per 10 ml of volume, dissolved in distilled water and adjusted to the mark. Due to the insufficient solubility of compound 1, another 10 ml of distilled water is added to the resulting volume of the solution.

Animals were clinically examined individually after administration for 30 minutes, then at least once per hour for 4 hours, then daily once a day for 14 days. Body mass was recorded immediately before the administration of the preparation to calculate the volume of administration, then once every two days.

Based on the conducted studies, it was found that compound 1 is low toxic, since the parameter $LD_{50}$ for oral administration in rats exceeds 5000 mg/kg of body weight.

Example 5. Determination of Acute Toxicity in Mice with Intraperitoneal Administration The study was performed on mice of the CD-1 (ICR) line (6-8 weeks, weight not less than 18 g) of both sexes. A single intraperitoneal injection of compound 1 was used at doses of 1000 mg/kg and 2000 mg/kg in a volume of 1 ml per 40 g of mouse body mass using an insulin syringe. The volume of administration was calculated individually for each animal, based on the body mass recorded immediately before the introduction of the substance.

To prepare a dose of 2000 mg/kg for administration to mice, a portion of 800 mg of compound 1 in a polystyrene boat on a Vibra scale (Shinko Denshi, Japan) was weighed, transferred to a volumetric flask of accuracy class A per 10 ml of volume, dissolved in physiological saline and adjusted to the mark. The solution was filtered with 0.22 µm syringe nozzles (Jet Biofil).

To prepare a dose of 1000 mg/kg for administration to mice, a portion of 400 mg of compound 1 in a polystyrene boat on a Vibra scale (Shinko Denshi, Japan) was weighed, transferred to a volumetric flask of accuracy class A per 10 ml of volume, dissolved in physiological saline and adjusted to the mark. The solution was filtered with 0.22 µm syringe nozzles (Jet Biofil).

Animals were clinically examined individually after administration for 30 minutes, then at least once per hour for 4 hours, then daily once a day for 14 days. Body mass was recorded immediately before the administration of the preparation to calculate the volume of administration, then once every two days.

Based on the conducted studies, it was found that compound 1 is low toxic, since the parameter $LD_{50}$ for intraperitoneal administration in rats exceeds 2000 mg/kg of body mass.

Thus, from the above it can be concluded that the claimed compound exhibits a high level of antiepileptic activity.

Thus, at doses of 25, 50 and 100 mg/kg, compound 1 completely suppresses the epileptic electrical activity of the brain within an hour after intraperitoneal administration to rats on the penicillin model of epilepsy.

The rats' corazol model of epilepsy shows a decrease in the intensity and duration of seizures with the administration of compound 1 at doses of 25 and 100 mg/kg intraperitoneally and 100 and 200 mg/kg orally, as well as the complete prevention of seizures in some cases at a dosage of 250 mg/kg with oral administration.

In this case, compound 1 is low toxic, since the $LD_{50}$ parameter in rats exceeds 2000 and 5000 mg/kg of body mass with intraperitoneal and oral administration, respectively.

In general, we can state that the applicant completed the tasks and achieved the claimed technical result, namely, a new compound was obtained that has high antiepileptic activity and has no analogues in the world in chemical structure. The resulting preparation will potentially significantly improve the quality and life expectancy of patients.

The claimed technical solution meets the criterion of "novelty" applied to the inventions, as the studied level of technology did not identify technical solutions that have the stated set of distinctive features that ensure the achievement of the stated results.

The claimed technical solution meets the criterion of "inventive step" applied to the inventions, as it is not obvious to a person skilled in this field of science and technology.

The claimed technical solution meets the criterion of "industrial applicability", as it can be implemented at any specialized enterprise using standard equipment, well-known domestic materials and technologies.

What is claimed is:
1. A pyridoxine-based compound of formula 1:
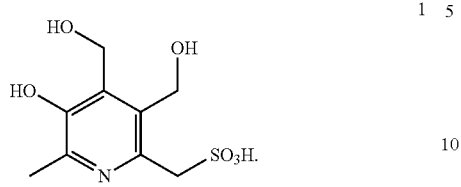
2. The pyridoxine-based compound according to claim 1, the compound having antiepileptic activity.